United States Patent
Manzer

(10) Patent No.: US 7,019,155 B2
(45) Date of Patent: Mar. 28, 2006

(54) HYDROGENATION OF TETRAHYDROXYBUTANE TO TETRAHYDROFURAN

(75) Inventor: Leo Ernest Manzer, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 0 days.

(21) Appl. No.: 10/292,881

(22) Filed: Nov. 12, 2002

(65) Prior Publication Data

US 2003/0149283 A1    Aug. 7, 2003

Related U.S. Application Data

(60) Provisional application No. 60/348,862, filed on Nov. 13, 2001.

(51) Int. Cl.
*C07D 307/02* (2006.01)

(52) U.S. Cl. .................. 549/509; 549/505; 549/507

(58) Field of Classification Search ............... 549/509, 549/505, 507

See application file for complete search history.

(56) References Cited

U.S. PATENT DOCUMENTS

| 4,313,884 A | 2/1982 | Arena |
| 4,401,823 A | 8/1983 | Arena |
| 4,939,277 A | 7/1990 | Imaki et al. |
| 6,013,812 A | 1/2000 | Haas et al. |
| 6,593,481 B1 * | 7/2003 | Manzer ............... 549/509 |

OTHER PUBLICATIONS

Hudson, B. G. and Barker, Robert, The Conversion of Accylic Carbohydrates of Tetrahydrofuran Derivatives. The Acid-Catalyzed Degydration of Tetritols and Pentitols, Journal of Organic Chemistry, 1967, 32, 11, p3650-3658.

Montassier, C, Ménézo, J. C., Moukolo, J., Naja, J., Hoang, L. C., Barbier, J. and Boitiaux, J. P., Polyol conversions into furanic derviatives on bimetallic catalysts: Cu-Ru, Cu-Pt and Ru-Cu, Journal of Molecular Catalysis, 1991, 70, p65-84, Elsevier Sequola, Lausanne.

Braca, Giuseppe, Raspolli, Anan Maria and Sbrana, Glauco, Anionic ruthenium Iodocarbonyl complexes as selective dehydroxylation catalysis in aqueous solution. Journal or Organometallic Chemistry, 1991, 417, 41-49, Elsevier Sequoia S.A.

* cited by examiner

*Primary Examiner*—Kamal A. Saeed
*Assistant Examiner*—Robert Shiao
(74) *Attorney, Agent, or Firm*—Charles E. Krukiel

(57) ABSTRACT

Disclosed is a method for the hydrogenation of tetrahydroxybutane in the presence of supported rhenium catalysts and an acid to form tetrahydrofuran and its precursors.

25 Claims, No Drawings

HYDROGENATION OF TETRAHYDROXYBUTANE TO TETRAHYDROFURAN

FIELD OF INVENTION

Tetrahydroxybutane is hydrogenated in the presence of supported rhenium catalysts to form tetrahydrofuran and its precursors.

BACKGROUND

Tetrahydrofuran (tetrahydrofuran) is an industrially important solvent and monomer. It is prepared commercially from nonrenewable petrochemical feedstocks. With the potential depletion of the world's oil reserves, a need exists to develop a source of tetrahydrofuran from renewable sources such as biomass. Biomass comprises primarily a carbohydrate containing material. Biomass can also mean as comprising a polysaccharide material. It can also mean comprising cellulose, hemicellulose, or lignocellulose materials: for example, the biomass as obtained from wood, plants, residue from agriculture or forestry, organic component of municipal and industrial wastes, primary sludges from paper manufacture, waste paper, waste wood (e.g., sawdust), agricultural residues such as corn husks, corn cobs, rice hulls, straw, bagasse, starch from corn, wheat oats, and barley, waste plant material from hard wood or beech bark, fiberboard industry waste water, bagasse pity, bagasse, molasses, post-fermentation liquor, furfural still residues, aqueous oak wood extracts, rice hull, oats residues, wood sugar slops, fir sawdust, naphtha, corncob furfural residue, cotton balls, rice, straw, soybean skin, soybean oil residue, corn husks, cotton stems, cottonseed hulls, starch, potatoes, sweet potatoes, lactose, waste wood pulping residues, sunflower seed husks, hexose sugars, pentose sugars, sucrose from sugar cane and sugar beets, corn syrup, hemp, and combinations of the above. Carbohydrates offer a convenient starting material, with their multiple reactive hydroxyl groups, but a drawback of using most carbohydrates is the need to remove the unwanted hydroxyls.

1,2,3,4-Tetrahydroxybutane, shown below, is a 4-carbon sugar alcohol, or tetritol and can have three isomeric forms: erythritol, the meso form; D-threitol and L-threitol:

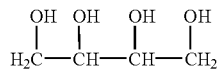

Erythritol is used as a low calorie sweetener and sugar substitute and is typically produced commercially via the fermentation of corn starch. Threitol has limited commercial manufacture or use, but can be produced via modification of the equivalent isomer of tartaric acid.

U.S. Pat. No. 4,939,277 and Hudson et al. (J. Org. Chem. (1967), 32(11), p3650) both describe the acid catalyzed cyclodehydration of erythritol, and Montassier, et al., (J. Mol. Catal. (1991), 70(1), p65) describe the Ru/Cu catalyzed reaction. Produced is dihydroxytetrahydrofuran, but not tetrahydrofuran. Braca, et al, (J. Organomet. Chem. (1991), 417(1–2), p41) disclose less than 4% of tetrahydrofuran in the homogenous Ru catalyzed cyclodehydration of erythritol.

U.S. Pat. No. 6,013,812 describes a process for the cyclodehydration of a 4-carbon polyol in the presence of a supported metal catalyst, an acid catalyst and added water, producing a mixture of various hydroxylated cyclic ethers. U.S. Pat. No. 4,401,823 uses carbonaceous pyropolymer impregnated with a transition metal to hydrogenate polyols to produce a large variety of compounds. U.S. Pat. No. 4,313,884 prepares anhydropolyols from the corresponding polyols using various metal ions as catalysts; however no examples are described using either Re salts or erythritol.

SUMMARY OF THE INVENTION

The invention is directed to a process for preparing tetrahydrofuran or a mixture of tetrahydrofuran and unsaturated precursors of tetrahydrofuran, the process comprising contacting 1,2,3,4-tetrahydroxybutane in the presence of at least one acid with a catalytic amount of rhenium, the rhenium being supported on a carbon support.

The particularly preferred process to prepare tetrahydrofuran and precursors to tetrahydrofuran comprises contacting erythritol in the presence of an acid with a catalytic amount of rhenium supported on carbon. The invention may further comprise the conversion of the precursors to tetrahydrofuran. Additionally, the catalyst may comprise the presence of a metal promoter on the carbon support, preferably selected from Group 8 metals of the Periodic Table of Elements, more preferably Ni or Pd.

In a preferred embodiment of the process of the invention, the acid is a) an acid with a $pK_a$ less than about 4, or a metal salt thereof, b) an acidic zeolite, or c) a mixture or one or more compounds from group a) with one or more compounds from group b). Preferably the acid of group a) is selected from the group consisting of inorganic acids, organic sulfonic acids, heteropolyacids, perfluoroalkyl sulfonic acids, and metal salts thereof. Preferably the acid is sulfuric acid, a sulfonic acid, or a fluorinated sulfonic acid polymer; more preferably the acid is sulfuric acid, methanesulfonic acid, p-toluicsulfonicacid, benzenesulfonic acid, a fluorinated sulfonic acid polymer ion-exchanged with a metal from Periodic Group 8, CBV-760 zeolite, CBV-1502 zeolite, CBV-400 zeolite, CBV-3020 zeolite, or 20A zeolite. The acid is optionally supported on a solid support.

In another embodiment of the process of the invention, the precursors of tetrahydrofuran are recycled back into the process for further conversion to tetrahydrofuran.

Also disclosed is a process for preparing tetrahydrofuran or a mixture of tetrahydrofuran and precursors of tetrahydrofuran, the process comprising the steps of:
  a) converting 1,2,3,4-tetrahydroxybutane to 3,4-tetrahydrofurandiol;
  b) optionally, separating the 3,4-tetrahydrofurandiol; and
  c) contacting the 3,4-tetrahydrofurandiol in the presence of at least one acid with a catalytic amount of rhenium, the rhenium being supported on a carbon support.

In preferred embodiment, the process is useful for preparing tetrahydrofuran and precursors to tetrahydrofuran comprising the steps of:
  a) converting erythritol to anhydroerythritol;
  b) optionally separating the anhydroerythritol; and
  c) contacting the anhydroerythritol in the presence of an acid with a catalytic amount of rhenium supported on carbon.

DETAILED DESCRIPTION OF THE INVENTION

The invention is a process to prepare tetrahydrofuran and its precursors by contacting tetrahydroxybutane in the presence of an acid with a catalytic amount of rhenium supported on carbon. By "tetrahydroxybutane" as used herein is meant any optical isomer, or mixture thereof, of 1,2,3,4-tetrahydroxybutane (1,2,3,4-butanetetrol). These isomers include erythritol, D-threitol and L-threitol. A preferred isomer is erythritol. By "precursors" as used herein is meant butanediol, unsaturated furans, and hydroxylated forms of tetrahydrofuran and unsaturated furans, and their isomeric forms, as represented by Formulae I, II, and III below, wherein each R is independently hydrogen or OH. Preferred precursors are furan and 1,4-dihydrofuran.

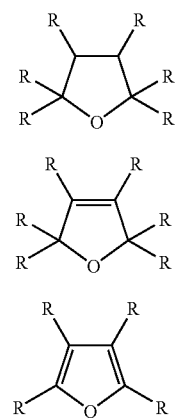

The process of the instant invention may further comprise the conversion of the precursors to tetrahydrofuran. This may be done by any of the numerous methods known in the art. See Ullmann's Encyclopedia of Industrial Chemistry, 5$^{th}$ Ed., Vol. A26, pp. 222–223 for a description of many of these methods. The instant process may also comprise the recycling of the precursors back into the process, for further conversion to tetrahydrofuran.

The process of the instant invention may additionally comprise converting tetrahydroxybutane to 3,4-tetrahydrofurandiol; optionally separating the 3,4-tetrahydrofurandiol; and then contacting the 3,4-tetrahydrofuraniol in the presence of an acid with a catalytic amount of rhenium supported on carbon to prepare tetrahydrofuran and unsaturated precursors to tetrahydrofuran. Tetrahydroxybutane is defined as described above. The conversion of tetrahydroxybutane to 3,4-tetrahydrofurandiol may be done by any method known in the art. See Advances in Carbohydrate Chemistry, S. Soltzberg, Vol. 25, pg. 229–231, 1970 for a description of many of these methods. The tetrahydrofurandiol may be isolated before contact with the catalyst; this can be done by any method known in the art, such as distillation, decantation, recrystallization, or extraction. A preferred embodiment comprises the conversion of erythritol to anhydroerythritol.

The catalysts of the present invention comprise rhenium supported on carbon. Preferably the catalyst contains about 1% to about 50% by weight of Re; more preferably about 5% to about 20%. Preferred carbons are those with a surface area >200 m$^2$/gm. The catalyst support can be in the form of powder, granules, pellets, or the like. Selection of an optimal average particle size for the catalyst will depend upon such process parameters as reactor residence time and desired reactor flow rates.

The catalyst can optionally contain a promoter, preferably a metal from Periodic Group 8 (Fe, Co, Ni, Ru, Rh, Pd, Os, Ir, and Pt). Preferred are Pd and Ni. The relative percentages of the catalyst promoter may vary, but should preferably be less than or equal to 50% of the catalytic metal. The catalyst also preferably should contain about 0.1% to about 5% by weight of the promoter metal; more preferably about 1%.

The catalyst can be prepared by any method known in the art. One preferred method involves impregnating the catalyst support by incipient wetness with one or more metal salts, followed by calcination.

Suitable acids are those with a pK$_a$ less than about 4, preferably with a pKa less than about 2, and can be a Brönsted or Lewis acid. They can include inorganic acids, organic sulfonic acids, heteropolyacids, perfluoroalkyl sulfonic acids and mixtures thereof. Also suitable are metal salts of acids with a pKa less than about 4, including metal sulfonates, metal trifluoroacetates, metal triflates, and mixtures thereof including mixtures of the salts with their conjugate acids. Specific examples of catalysts include sulfuric acid, fluorosulfonic acid, phosphoric acid, p-toluenesulfonic acid, benzenesulfonic acid, phosphotungstic acid, phosphomolybdic acid, trifluoromethanesulfonic acid, methanesulfonic acid, p-toluicsulfonic acid, 1,1,2,2-tetrafluoroethanesulfonic acid, 1,1,1,2,3,3-hexafluoropropanesulfonic acid, and triflatic acid and its salts. Sulfonic acids are compounds with at least one —SO$_2$H group or its salt. Examples of preferred sulfonic acids include methanesulfonic acid, p-toluicsulfonic acid, and benzenesulfonic acid. By acidic zeolites, it is meant a zeolite with labile H$^+$ groups or Lewis acid sites on its surface.

Fluorinated sulfonic acid polymers are partially or totally fluorinated hydrocarbon polymers containing pendant sulfonic acid groups, which may be partially or totally converted to the salt. One particularly suitable fluorinated sulfonic acid polymer is Nafion® perfluorinated sulfonic acid polymer, (E.I. DuPont de Nemours, Wilmington, Del.). One preferred form is Nafion® Super Acid Catalyst, a bead-form strongly acidic resin which is a copolymer of tetrafluoroethylene and perfluoro-3,6-dioxa-4-methyl-7-octenesulfonyl fluoride, converted to either the proton (H+) or the metal salt form.

The acid can be optionally supported on a suitable solid support. Suitable solid supports include but are not limited to SiO$_2$ (silica), Al$_2$O$_3$ (alumina), TiO$_2$ (titania), MgO (magnesia) or ZrO$_2$ (zirconia), zeolites, carbon, clays, or mixtures thereof. Any method known in the art to prepare the supported catalyst can be used. One preferred supported acid is Nafion® on silica.

The process of the invention is preferably performed in the liquid phase, and can be performed in any suitable reactor such as but not limited to a fixed bed, slurry, fixed plug, and a trickle bed reactor system. The reaction temperature is preferably about 100° C. to about 300° C., more preferably about 150° C. to about 250° C., most preferably 200° C. The process of the present invention may be performed at pressures of 1.0 MPa to 10.0 MPa. The process is preferably performed at pressures of ambient to about 1000 psi (6.9 MPa), most preferably at about 500 psi (3.5 MPa).

The choice of solvent or mixture of solvents is not critical provided the solvent is not detrimental to catalyst, reactant and product. The solvent can also consist partially or totally of the recycled precursors.

It will be appreciated that the selectivities and yields of product may be enhanced by additional contact with the catalyst. For example, yields and selectivities may be increased where the reactor effluent containing a mixture of reactant and product may be passed one or more times over the catalyst under the reaction conditions to enhance the conversion of reactant to product.

The process of the instant invention may additionally comprise the recovery or isolation of tetrahydrofuran and optionally one or more of the precursors. This can be done by any method known in the art, such as distillation, decantation, recrystallization, or extraction.

Materials and Methods
The following abbreviations are used herein:

| | |
|---|---|
| AERY | Anhydroerythritol |
| BDO | Butanediol |
| BSA | Benzene sulfonic acid |
| DHF | 1,4-Dihydrofuran |
| FUR | Furan |
| GBL | Gamma-butyrolactone |
| GC/Mass | Gas chromatograph/mass spectrometer |
| MSA | Methanesulfonic acid |
| PTA | p-Toluicsulfonic acid |
| SAC | Nafion ® Superacid Catalyst-13 |
| THF | Tetrahydrofuran |
| TOT | Total tetrahydrofuran and precursors |
| Support | Source |
| Sibunit carbon | Boreskov Inst. of Catalysis, Novosibirsk, Russia |
| Calsicat carbon | Englehard Corp., E. Windsor, CT |
| Calgon PCB carbon | Calgon Corp. Pittsburgh, PA |

EXAMPLES

The catalysts were prepared using the following general procedure. Where indicated in the table below, the carbon support was first dried and reduced under an atmosphere of $H_2$ for 2 hours at the temperatures indicated. Unless otherwise specified in the Table, the carbon used was Calgon PCB. In a 150 ml beaker, a solution or slurry was made up of the metal precursors and deionized $H_2O$. The precursors used were $NiCl_2 \cdot 6H_2O$ (available from Alfa Aesar, Ward Hill, Mass.), $PdCl_2$ (Alfa), and $Re_2O_7$ (Alfa). The carbon support was added to the slurry. The slurry was allowed to stand at for 1 hour at room temperature with occasional stirring and then dried at 120° C. overnight with frequent stirring (until free flowing).

CBV-760 zeolite was obtained from PQ Corporation, P O Box 842, Valley Forge Pa. 19482, lot number7600510711, granulated to 16/20 mesh. CBV-3020E zeolite was obtained from PQ Corporation, P O Box 842, Valley Forge Pa. 19482, lot number 1525-51] and calcined by heating in flowing air at 1° C./min to 500° C., held at 500° C. for 5 hr., then cooled to 110° C. CBV-400 was obtained from Conteka, Leiden, Netherlands, now part of Zeolyst International, Valley Forge, Pa., lot number 39-09-004, granulated to 16/20 mesh. CBV-1502 zeolite was obtained from Conteka, Leiden, Netherlands, now part of Zeolyst International, Valley Forge, Pa., lot number 39-90-003, and calcined by heating in flowing air at 1° C./min to 500° C., held at 500° C. for 5 hr, then cooled to 110° C. Valfor CBV-20A zeolite was obtained from PQ Corporation, P O Box 842, Valley Forge Pa. 19482, lot number AD-29-1, and calcined by heating in flowing air at 1° C./min to 500° C., held at 500° C. for 5 hr, then cooled to 110° C.

The 13% Nafion® on $SiO_2$ was prepared as follows. Nafion® PFIEP solutions can be purchased from Aldrich Chemical Co., Milwaukee, Wis., or PFIEP solutions generally can be prepared using the procedure of U.S. Pat. No. 5,094,995 and U.S. Pat. No. 4,433,082. Unless otherwise noted, the Nafion® PFIEP solution referred to in the examples is Nafion® NR 005, a Nafion® solution available from DuPont Nafion® Products, Fayetteville, N.C., and also known as Nafion® SE-5110, and is prepared from resin which is approximately 6.3 (TFE) molecules for every perfluoro(3,6-dioxa-4-methyl-7-octenesulfonyl fluoride) molecule $(CF_2 = CFO[CF_2CF(CF_3)]OCF_2CF_2SO_2F$ (PSEPVE)) and has an equivalent weight of approximately 1070.

13.5 wt. % Nafion® PFIEP in silica, with pore diameter about 10 nm, 204 g of tetramethoxysilane (TMOS), 33 g of distilled water and 3 g of 0.04M HCl was stirred for 45 min to give a clear solution. To 300 mL of a Nafion® solution (which contains 5% of Nafion® PFIEP by weight) was added 150 mL of a 0.4 M NaOH solution, while the Nafion® solution was being stirred. After addition of the sodium hydroxide solution, the resulting solution was stirred for a further 15 min. The silicon containing solution, prepared as described above, was added rapidly to the stirred Nafion® containing solution. After about 10–15 seconds, the solution gelled to a solid mass. The gel was placed in an oven and dried at a temperature of about 95° C., over a period of about 2 days, followed by drying under vacuum overnight. The hard glass-like product was ground and passed through a 10-mesh screen. The material was then stirred with 3.5 M HCl for 1 hour (with 500 mL of acid), followed by washing with 500 mL of deionized water. The solid was collected by filtration. Acidification, washing and filtration were repeated a total of 5 times and after the final wash the solid was dried under vacuum at 100° C. for 24 hours. Yield of dried product was 98 g. The metal-exchanged Nafion® was prepared by adding about 50 g of the Nafion® Superacid Catalyst-13 to 75 g of water containing either 0.4 g of $Pd(NO_3)_2 \cdot H_2O$ or 0.15 g of $RhCl_3 \cdot H_2O$. The solutions sat overnight, then were washed with distilled water before being dried in vacuum at 110° C. overnight. These are indicated.

The reaction was performed by placing 50 mg of erythritol (meso form, Aldrich), 50 mg of catalyst, 50 mg of the acid, and 1 ml of dioxane solvent in a 2 ml pressure vessel. The vessel was pressurized with $H_2$ to 500 psi (3.4 MPa), and then the vessel was heated to reaction temperature for 2 hours. The vessel was then cooled, methoxyethylether was added as an internal standard and the products analyzed on an HP 6890 GC/Mass using a column of CP-Wax 58 (FFAP) 25 m×0.25 mm ID from Chrompack. By relating the areas of individual components relative to the internal standard and applying response factors, the yield (Yld) of each individual product was calculated, as set forth in the Table as follows.

TABLE

| Ex. | Catalyst | Acid | FUR Yld (%) | THF Yld (%) | DHF Yld (%) | TOT Yld (%) | GBL Yld (%) | BDO Yld (%) | AERY Yld (%) |
|---|---|---|---|---|---|---|---|---|---|
| 1 | 10% Re/1% Pd/C | 13% Nafion ®/SiO$_2$ | 0.4 | 49.8 | 0 | 50.2 | 3.0 | 0.0 | 0.0 |
| 2 | 10% Re/1% Pd/C | Rh/SAC | 0.9 | 46.1 | 0 | 47.0 | 4.2 | 0.0 | 0.0 |

TABLE-continued

| Ex. | Catalyst | Acid | FUR Yld (%) | THF Yld (%) | DHF Yld (%) | TOT Yld (%) | GBL Yld (%) | BDO Yld (%) | AERY Yld (%) |
|---|---|---|---|---|---|---|---|---|---|
| 3 | 10% Re/1% Pd/C | Pd/SAC | 1.1 | 43.8 | 0 | 44.9 | 3.2 | 0.0 | 0.0 |
| 4 | 10% Re/1% Ni/C | 13% Nafion ®/SiO₂ | 0.4 | 41.5 | 0.1 | 42.0 | 0.9 | 0.1 | 0.0 |
| 5 | 20% Re/Calsicat C | Rh/SAC | 0.8 | 36.9 | 5.6 | 43.3 | 5.5 | 0.2 | 6.1 |
| 6 | 10% Re/1% Ni/C | Rh/SAC | 0.5 | 34 | 0.1 | 34.6 | 1.0 | 0.1 | 0.0 |
| 7 | 20% Re/Calsicat C | Pd/SAC | 0.7 | 30.2 | 4.1 | 35.0 | 4.5 | 0.3 | 1.7 |
| 8 | 20% Re/Calsicat C | 13% Nafion ®/SiO₂ | 0.6 | 29.7 | 5 | 35.3 | 6.0 | 0.3 | 4.6 |
| 9 | 20% Re/Calsicat C | Pd/SAC | 0.9 | 27.6 | 4.8 | 33.3 | 4.3 | 0.1 | 3.3 |
| 10 | 20% Re/Calsicat C | 13% Nafion ®/SiO₂ | 0.6 | 27.6 | 4.4 | 32.6 | 5.1 | 0.2 | 1.5 |
| 11 | 10% Re/Calsicat C | Pd/SAC | 8.4 | 27.2 | 7.7 | 43.3 | 3.9 | 0.0 | 2.3 |
| 12 | 10% Re/1% Ni/C | Pd/SAC | 0.7 | 26.8 | 0.2 | 27.7 | 1.4 | 0.2 | 0.0 |
| 13 | 20% Re/Calsicat C | Rh/SAC | 0.7 | 26.7 | 5.5 | 32.9 | 4.6 | 0.1 | 2.8 |
| 14 | 10% Re/Calsicat C | Pd/SAC | 5.2 | 25.4 | 6.4 | 37.0 | 4.6 | 0.0 | 4.9 |
| 15 | 10% Re/Calsicat C | 13% Nafion ®/SiO₂ | 10.4 | 23.3 | 5.1 | 38.8 | 3.2 | 0.1 | 0.2 |
| 16 | 10% Re/Calsicat C | Rh/SAC | 10.2 | 22.1 | 8.1 | 40.4 | 4.0 | 0.0 | 3.2 |
| 17 | 10% Re/Calsicat C | 13% Nafion ®/SiO₂ | 7.7 | 21.4 | 7 | 36.1 | 4.8 | 0.0 | 5.7 |
| 18 | 10% Re/Calsicat C | Rh/SAC | 6.9 | 21.3 | 6.5 | 34.7 | 4.4 | 0.0 | 7.7 |
| 19 | 20% Re/Calsicat C | CBV-760 Zeolite | 8 | 20.9 | 1.7 | 30.6 | 5.6 | 0.0 | 5.1 |
| 20 | 20% Re/Sibunit C | Pd/SAC | 3.5 | 15.5 | 5.2 | 24.2 | 2.7 | 0.0 | 17.8 |
| 21 | 5% Re/Calsicat C | Pd/SAC | 5.4 | 15.2 | 5.2 | 25.8 | 3.2 | 0.0 | 13.5 |
| 22 | 20% Re/Calsicat C | CBV-1502 Zeolite | 10.5 | 14.6 | 6.8 | 31.9 | 5.3 | 0.0 | 1.9 |
| 23 | 20% Re/Sibunit C | Rh/SAC | 4.1 | 14.1 | 6 | 24.2 | 3.2 | 0.2 | 21.1 |
| 24 | 20% Re/Calsicat C | CBV-400 Zeolite | 6.9 | 13.1 | 1.3 | 21.3 | 3.9 | 0.0 | 2.7 |
| 25 | 5% Re/Calsicat C | Pd/SAC | 4.3 | 12.3 | 4.5 | 21.1 | 2.9 | 0.0 | 23.3 |
| 26 | 20% Re/Sibunit C | 13% Nafion ®/SiO₂ | 4.6 | 12.2 | 11.5 | 28.3 | 2.7 | 0.5 | 24.1 |
| 27 | 20% Re/Sibunit C | Pd/SAC | 2 | 11.2 | 3.4 | 16.6 | 1.9 | 0.0 | 19.4 |
| 28 | 5% Re/Calsicat C | Rh/SAC | 7.2 | 10.8 | 5.5 | 23.5 | 3.2 | 0.1 | 15.5 |
| 29 | 20% Re/Sibunit C | 13% Nafion ®/SiO₂ | 3.2 | 10.5 | 3.9 | 17.6 | 1.9 | 0.3 | 19.0 |
| 30 | 5% Re/Calsicat C | 13% Nafion ®/SiO₂ | 5.3 | 8.7 | 3.8 | 17.8 | 3.1 | 0.2 | 23.3 |
| 31 | 5% Re/Calsicat C | 13% Nafion ®/SiO₂ | 7.9 | 8.7 | 3.3 | 19.9 | 2.7 | 0.3 | 17.7 |
| 32 | 20% Re/Sibunit C | Rh/SAC | 3.3 | 8.6 | 4.9 | 16.8 | 1.6 | 0.2 | 22.0 |
| 33 | 5% Re/Calsicat C | 13% Nation ® | 1.3 | 8.1 | 3 | 12.4 | 0.0 | 0.0 | 7.1 |
| 34 | 20% Re/Calsicat C | 20A Zeolite | 0.9 | 8 | 3.5 | 12.4 | 3.7 | 0.1 | 19.0 |
| 35 | 5% Re/Calsicat C | Rh/SAC | 5.6 | 8 | 4.7 | 18.3 | 2.4 | 0.1 | 23.7 |
| 36 | 20% Re/Calsicat C | CBV-3020 Zeolite | 11.2 | 7.6 | 9.6 | 28.4 | 4.0 | 0.0 | 2.0 |
| 37 | 5% Re/Calsicat C | MSA | 6 | 5.4 | 4.8 | 16.2 | 0.0 | 0.0 | 5.7 |
| 38 | 5% Re/Calsicat C | 20A Zeolite | 4.5 | 3.2 | 10.3 | 18.0 | 0.0 | 0.0 | 11.8 |
| 39 | 5% Re/Calsicat C | BSA | 1.4 | 2.8 | 0.7 | 4.9 | 0.0 | 0.0 | 14.4 |
| 40 | 5% Re/Calsicat C | H₂SO₄ | 3 | 1 | 0.4 | 4.4 | 0.0 | 0.0 | 87.3 |
| 41 | 5% Re/Calsicat C | PTA | 1.8 | 0.7 | 1.4 | 3.9 | 0.0 | 0.0 | 1.5 |

What is claimed is:

1. A process for preparing tetrahydrofuran or a mixture of tetrahydrofuran and unsaturated compounds having either one of Formulae II or III,

II

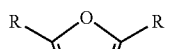

III wherein R is independently hydrogen or —OH, the process comprising:
contacting 1,2,3,4-tetrahydroxybutane in the presence of at least one acid with a catalytic amount of rhenium, the rhenium being supported on a carbon support.

2. The process according to claim 1 wherein the 1,2,3,4-tetrahydroxybutane is erythritol.

3. The process according to claim 1 further comprising converting said unsaturated compounds of formula (II) or (III) to tetrahydrofuran.

4. The process of claim 3 wherein the unsaturated compounds of formula (II) or (III) are recycled back into said process.

5. The process according to claim 1 wherein the rhenium supported on the carbon support further comprises a metal promoter.

6. The process according to claim 5 wherein the metal promoter is selected from Group 8 metals of the Periodic Table of Elements.

7. The process according to claim 3 wherein the metal promoter is Ni or Pd.

8. The process according to claim 1 wherein the acid is selected from the group consisting of a) an acid having a pK$_a$ less than about 4, or a metal salt thereof, b) an acidic zeolite, and c) a mixture of one or more compounds from a) with one or more compounds from b).

9. The process of claim 1 wherein the acid comprises at least one compound selected from the group consisting of inorganic acids, organic sulfonic acids, heteropolyacids, perfluoroalkyl sulfonic acids, and metal salts thereof.

10. The process according to claim 1 wherein the acid comprises at least one compound selected from the group consisting of sulfuric acid, sulfonic acid, and fluorinated sulfonic acid polymer.

11. The process according to claim 1 wherein the acid comprises at least one compound selected from the group consisting of sulfuric acid, methanesulfonic acid, p-toluic-sulfonic acid, benzenesulfonic acid, fluorinated sulfonic acid polymer ion-exchanged with a metal from Group 8 of the Periodic Table of Elements, a zeolite with labile H+ groups on its surface, and a zeolite with Lewis acid sites on its surface.

12. The process according to claim 1 wherein the acid is supported on a solid support.

13. The process according to claim 12 wherein the solid support is selected from the group consisting of $SiO_2$ (silica), $Al_2O_3$ (alumina), $TiO_2$ (titania), MgO (magnesia) or $ZrO_2$ (zirconia), zeolites, carbon, clays, and mixtures thereof.

14. The process according to claim 1 wherein the process is performed at a temperature of 100° C. to 300° C. and a pressure of 1.0 MPa to 10.0 MPa.

15. The process according to claim 1 wherein the process is performed at a temperature of 150° C. to 250° C. and a pressure of 3.0 MPa to 4.0 MPa.

16. The process according to claim 1, wherein the process is performed in the presence of a solvent, and wherein further the solvent is a dioxane solvent.

17. The process according to claim 1 wherein the mixture of tetrahydrofuran and one or more unsaturated compounds of formula (II) or (III) is prepared.

18. A process for preparing a compound having any one of Formulae I, II or III:

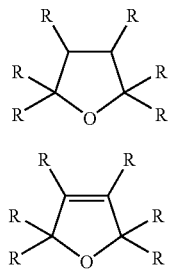

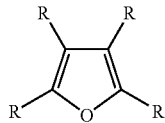

wherein R is independently hydrogen or hydroxyl group, the process comprising:
  contacting 1,2,3,4-tetrahydroxybutane in the presence of at least one acid with a catalytic amount of rhenium, the rhenium being supported on a carbon support.

19. The process of claim 1 wherein the process is performed in the presence of a solvent.

20. The process of claim 1 wherein the acid has a pKa less than about 2.

21. The process of claim 1 wherein the catalyst comprises about 1% to about 50% by weight of rhenium.

22. The process of claim 21 wherein the catalyst comprises about 5% to about 20% by weight of rhenium.

23. The process of claim 1 further comprising contacting the tetrahydroxybutane with a catalytic amount of rhenium in the presence of hydrogen.

24. The process according to claim 19, wherein the solvent is a dioxane solvent.

25. A process for producing a composition comprising tetrahydrofuran, furan, and 1,4-dihydrofuran, the process comprising:
  contacting 1,2,3,4-recrahydroxybutane in the presence of at least one acid with a catalytic amount of rhenium, the rhenium being supported on a carbon support.

* * * * *